United States Patent [19]
Abela

[11] Patent Number: 4,860,743
[45] Date of Patent: Aug. 29, 1989

[54] LASER METHOD AND APPARATUS FOR THE RECANALIZATION OF VESSELS AND THE TREATMENT OF OTHER CARDIAC CONDITIONS

[75] Inventor: George S. Abela, Gainesville, Fla.

[73] Assignee: University of Florida, Gainesville, Fla.

[21] Appl. No.: 56,878

[22] Filed: Jun. 3, 1987

Related U.S. Application Data

[63] Continuation-in-part of Ser. No. 924,292, Oct. 27, 1986, abandoned, which is a continuation of Ser. No. 757,778, Jul. 24, 1985, abandoned, which is a continuation of Ser. No. 559,722, Dec. 9, 1983, abandoned.

[51] Int. Cl.[4] .............................................. A61B 17/36
[52] U.S. Cl. .................................................. 128/303.1
[58] Field of Search ........................................ 128/4–8, 128/303.1, 395–398, 734

[56] References Cited

U.S. PATENT DOCUMENTS

| | | | |
|---|---|---|---|
| 1,791,794 | 2/1931 | Chesney | 128/398 |
| 4,224,949 | 9/1980 | Scott et al. | 128/734 |
| 4,445,892 | 5/1984 | Hessein et al. | 128/303.1 |
| 4,512,762 | 4/1985 | Spears . | |
| 4,551,129 | 11/1985 | Coleman et al. | 128/303.1 |
| 4,612,938 | 9/1986 | Dietrich et al. | 128/303.1 |
| 4,646,737 | 3/1987 | Hussein . | |
| 4,660,925 | 4/1987 | McCaughan | 128/303.1 |
| 4,662,368 | 5/1987 | Hussein et al. | 128/303.1 |
| 4,672,961 | 6/1987 | Davies | 128/303.1 |
| 4,676,231 | 1/1987 | Hisazumi et al. | 128/303.1 |
| 4,693,244 | 9/1987 | Daikuzono | 128/303.1 |
| 4,693,556 | 9/1987 | McCaughan | 128/303.1 |

*Primary Examiner*—Max Hindenburg
*Attorney, Agent, or Firm*—Dennis P. Clarke

[57] ABSTRACT

Cardiac conditions such as blockages in arteries caused by plaque build-up are treated intravascularly with laser radiation using an optical fiber having a heat conducting end cap on its distal end. A spherical lens within the end cap focuses a small portion of the laser energy directly into the plaque which is in contact with the tip of the end cap and disperses the remaining energy into the end cap for heating it up. The direct laser energy vaporizes part of the plaque so that the end cap can be easily forced through the blockage, and the tissue in contact with the heated end cap is burned away. A diffuser catheter for the ablation of electrical conduction tissue in the heart employs spaced electrodes for detecting the presence of the conduction tissue, and directs laser energy outwardly through the side of the catheter for vaporizing the tissue.

10 Claims, 4 Drawing Sheets

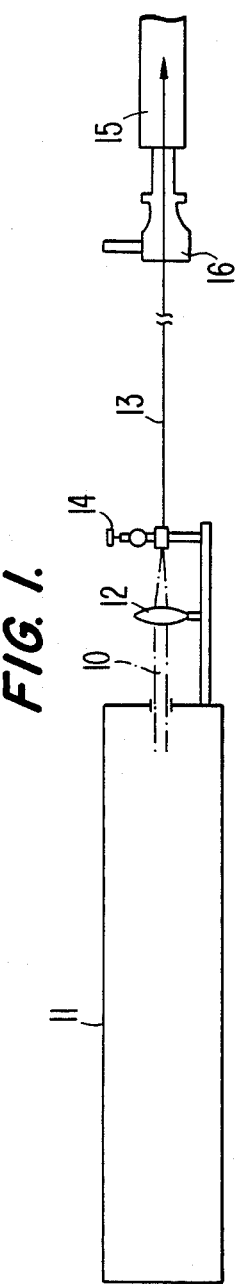
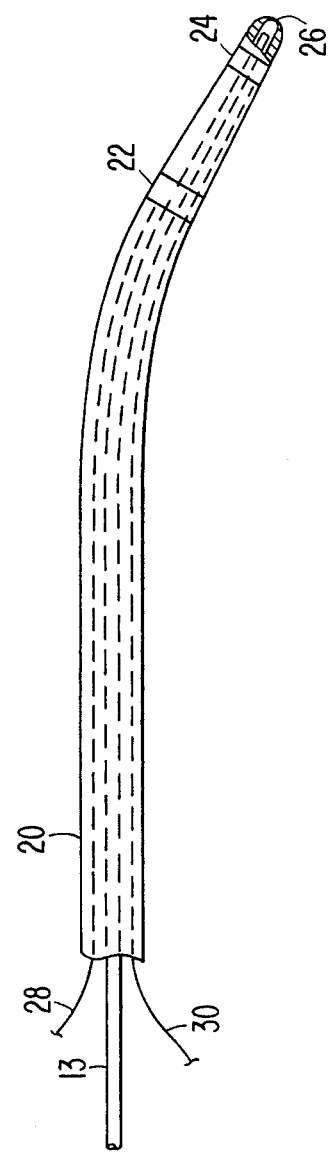
FIG. 1.
FIG. 2.

LASER METHOD AND APPARATUS FOR THE RECANALIZATION OF VESSELS AND THE TREATMENT OF OTHER CARDIAC CONDITIONS

This application is a continuation-in-part of prior application Ser. No. 924,292, filed Oct. 27, 1986, (abandoned) which is a continuation of application Ser. No. 757,778, filed July 24, 1985 (abandoned), which is a continuation of application No. 559,722, filed Dec. 9, 1983 (abandoned).

BACKGROUND OF THE INVENTION

Atherosclerosis is a major medical problem responsible for a degree of morbidity and mortality as a result of limb ischemia, stroke and myocardial infarction. Current revascularization therapies to relieve the condition include arterial bypass surgery, percutaneous transluminal angioplasty and thrombolysis of clot.

There are numerous disadvantages associated with these current methods for vascular reperfusion of an ischemic area. Cardiac artery bypass surgery and bypass surgery for ischemic limbs entails extensive and complicated surgery, and requires that the patient have adequate lung function and kidney function in order to tolerate the circulatory bypass necessary for the procedure. The complications associated with this surgery are directly related to the time that the patient is on circulatory bypass. These complications include strokes, renal failure, and ultimately the inability to resuscitate the heart. Other immediate complications of such surgery include strokes and heart attacks during or as a consequence of the surgery. Some patients are not relieved of their anginal symptoms after the bypass surgery, and some develop a graft closure immediately or within the first year following the procedure. Bypass grafting for ischemic limbs and threatened strokes entails prolonged and extensive surgery and is also greatly limited by the above-described complications.

More recently the development of balloon angioplasty utilizing a catheter device that can cross an obstructive intravascular lesion has permitted a less invasive approach with good results in a small percentage of patients without the necessity for the risk of major surgery. With this technique a balloon carried on the catheter is threaded across an obstruction of plaque and inflated to destroy the plaque. This technique, however, requires the ability to cross the obstruction with the catheter. Hard obstructions may be impossible to cross and are not generally successfully removed or destroyed by this technique. Moreover, because of the size of the catheter and balloon involved, the vessels that can be entered are limited to the larger or moderately large size vessels.

Laser radiation shares properties with regular light; however, its monochromaticity and coherence give it special characteristics. The property of monochromaticity of the laser allows differential absorption of various wavelengths by specific tissues. The coherence and high amplification of laser energy is a quality which makes the laser useful as a cutting or burning instrument. The cardiovascular applications for laser radiation have not been investigated until recently. Little is known about the long-term photobiological effects of laser radiation on vascular tissues and cells. However, because of its light properties, the laser beam is capable of delivery through flexible optical fibers made of silica or quartz which can be passed through vascular catheters and is, therefore, capable of being localized at various sites within the arteries and veins. This particular quality of laser energy, in addition to its ability to photocoagulate and cut tissues, makes it a potentially suitable instrument to open or widen obstructive lesions within the vascular system. There are, however, a number of problems with the intravascular use of laser radiation for the treatment of cardiovascular conditions, and these have, in the past, limited such use in humans.

A major recurring problem which has been encountered with the intravascular delivery of laser energy using optical fibers is vascular perforation. The manipulation of optical fibers inside arteries is difficult, and inadequate steerabilty and positioning of the fiber can result in mechanical perforation of the vessel wall as at curves or branches. Vascular perforation may also result from thermal damage to the vessel wall, as, for example, because of dispersion of the laser beam beyond the plaque or improper positioning of the optical fiber so that it directs laser energy directly into the vessel wall. The risk of mechanical perforation may be minimized by putting the optical fiber into a catheter system which has a steerable guide wire similar to that currently used for balloon angioplasty. Preventing thermal perforation of the vessel has been more difficult to achieve.

One known system attempts to avoid thermal perforation by employing the laser radiation solely for heating a metal tip on the end of the fiber and using the heated tip to burn through the plaque. While this technique may avoid perforation due to the laser beam impinging directly onto the vessel wall, it does not prevent thermal perforation. The tip itself may burn through the wall. Moreover, tissue, as of the vessel wall, may stick to the hot tip, causing the tissue to tear as the tip is moved and producing a thrombosis. This technique also requires mechanical pressure to force the tip through the plaque, and has not been very successful with blockages located at any substantial distance from the entry point of the catheter, or in small winding cardiac arteries, since sufficient mechanical pressure cannot be exerted on the tip to force it through the plaque.

Moreover, methods and systems proposed to date for the utilization of lasers to remove plaque from blood vessels require the exclusion of blood from the vessel in the area of the plaque and the necessity for providing means for removing debris from the vessel, such as by suction device, etc. Also, the destruction of a hard to remove material such as plaque without concomitant damage to the surrounding vessel walls has been difficult to achieve.

The properties of laser radiation offer the potential of its use for treating other cardiac conditions, such as for destroying abnormal conduction tissue in the heart, e.g., the bundle of His, or for the occlusion of undesirable vascular channels. There has, however, been no reported success in the utilization of laser systems for such purposes.

It is an object of the present invention to provide a method particularly adapted for the efficacious and safe recanalization of blood vessels obstructed by plaque with a laser which is not subject to the disadvantages discussed heretofore.

It is a further object of the invention to provide a method for the occlusion of undesirable cardiovascular channels employing a laser.

It is still a further object of the invention to provide a method for the revascularization of cardiovascular tissue employing a laser based system.

It is still a further object of the invention to provide a method for the location and destruction of conduction tissue in the heart utilizing a laser based system.

SUMMARY OF THE INVENTION

The invention affords an improved apparatus and method for the intravascular treatment of cardiac conditions using laser radiation which avoids the foregoing and other disadvantages of known apparatus and methods. In particular, the invention enables the recanalization of a blood vessel in a living being which is at least partially obstructed by plaque by employing a combination of direct laser radiation for vaporizing the plaque, thermal energy to afford a melting affect on the plaque, and mechanical pressure. The invention also provides for the ablation of electrical conduction tissue in the heart of a living being through the use of laser radiation to vaporize the conduction tissue. The invention further enables the occluding of undesirable cardiovascular channels through the use of laser radiation to burn and melt the tissue so as to close and obstruct the undesirable channel. In addition, the invention further enables revascularization of cardiovascular tissue by using it to destroy the tissue and create new channels or openings therein.

Briefly stated, in one aspect, the invention affords an apparatus and a method for the treatment of cardiac conditions wherein a catheter is inserted into a blood vessel and threaded through the vessel to a location which is to be treated, the catheter carrying an optical fiber having a proximal end and a distal end. A smoothly shaped end member formed of heat conductive material is disposed on the distal end of the fiber, the distal end terminating within the end member and the end member having an opening at a tip thereof for emitting laser radiation carried by the optical fiber. The laser radiation from the end of the optical fiber impinges upon lens means disposed within the end member such that a portion of the laser beam from the fiber is focused through the opening in the end member so as to impinge upon a point which is to be treated, and a second portion of the beam is dispersed by the lens means into the end member so as to produce heating of the end member.

In another aspect, a catheter may have an end cap formed of heat conductive material disposed on its distal end, and the end cap may have a plurality of channels extending through the end cap to corresponding openings at the tip of the end cap. One of the channels through the end cap may carry a guide wire for steering the catheter through the vessel, and the other channels may each carry an optical fiber which terminates in lens means disposed at the tip of the end cap, the lens means being formed to focus a first portion of the laser beam carried by such fiber through the corresponding opening in the cap and for dispersing a second portion of the laser beam into the end cap so as to cause heating of the end cap.

In yet another aspect, the invention provides an apparatus for treating cardiac conditions with laser radiation which comprises a catheter adapted to be inserted into an artery and threaded through the artery to a location to be treated, the catheter having a tubular body with a proximal end and a distal end, a window of laser radiation transparent material formed in a sidewall of the catheter, an optical fiber disposed within the catheter for guiding a laser beam and having an end terminating adjacent to the window, and lens means mounted on the end of the fiber for dispersing the laser beam carried by the fiber sideways and outwardly through the window for treating tissue adjacent to the window.

The invention further provides for the ablation of electrical conduction tissue in the heart of a living being by threading a catheter through an artery into the heart, the catheter having electrode means disposed thereon for detecting the presence of conduction tissue and a laser radiation transparent window disposed adjacent to the electrode means in a sidewall of the catheter. Upon detection, using the electrode means, of the presence of conduction tissue adjacent to the window, laser radiation emitted from an optical fiber carried within the catheter is caused to be directed outwardly through the window so as to produce vaporization of the adjacent conduction tissue.

The invention further provides for the occluding of an undesirable cardiovascular channel by threading a catheter carrying an optical fiber through a cardiac artery to the position of the undesirable channel, and exposing the tissue forming the channel to laser radiation emitted from the optical fiber so as to cause melting of the tissue and collapsing of channel walls to close the channel.

Finally, the invention enables the revascularizing of cardiovascular tissue by threading a catheter through an artery to a location to be treated, and exposing the tissue to laser radiation emitted from an optical fiber carried by the catheter so as to burn through the tissue and create a channel therein.

BRIEF DESCRIPTION OF THE DRAWINGS

FIG. 1 is a diagrammatic view of a laser/optical fiber/catheter apparatus which may be employed for practising the invention;

FIG. 2 is a fragmentary elevational view of one form of a optical fiber/catheter apparatus in accordance with the invention which is adapted to detect and destroy conduction pathways within the heart;

DESCRIPTION OF PREFERRED EMBODIMENTS

Figure 3:
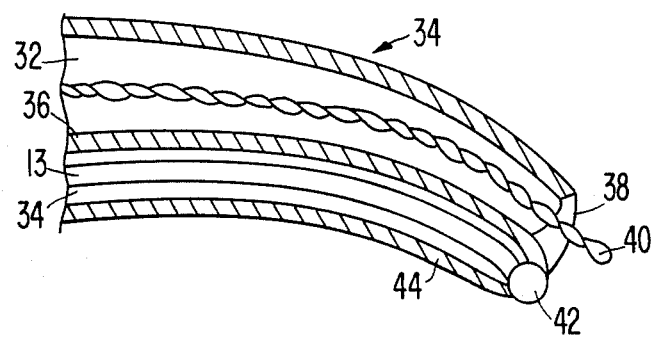
FIG. 3 is a partial sectional view of an embodiment of a laser catheter probe in accordance with the invention.

FIG. 1 illustrates, diagrammatically, a laser/optical fiber/catheter system which may be employed with the invention. As shown, laser radiation 10 produced by a laser source 11 may be beamed and focused by means of a lens 12 into the proximal end of an optical fiber 13 which is held and aligned with the beam by a positioning device 14, which may be a conventional X—Y—Z positioning adapter device. The optical fiber may be disposed within a catheter 15 which is adapted to be inserted into and threaded through appropriate blood vessels, such as arteries, to a site which is to be treated. The optical fiber serves as an optical waveguide which carries the laser beam intravascularly to the treatment site. As shown in the figure, fiber 13 may enter the proximal end of catheter 15 through a conventional hemostasis valve 16 or the like. The valve enables a solution, such as a contrast solution or saline flush to be delivered through the catheter to the treatment site, if desired, As will be explained in more detail shortly, the catheter may also carry a steerable guide wire to facilitate threading of the catheter through the blood vessels.

FIG. 2 illustrates generally one form which the distal end 20 of catheter 15 may take. The device illustrated in FIG. 2 is especially shaped and adapted to be threaded through appropriate arteries to the heart for the detection and localization of abnormal conduction pathways, such as the bundle of His. As shown, the end of the catheter may have a pair of spaced electrodes 22 and 24 encircling its peripheral surface adjacent to its tip 26. The electrodes 22 and 24 may be connected via electrical conduction leads 28 and 30, respectively, carried within the catheter to an electrocardiogram (not illustrated) for detection of the conduction pathways in a conventional manner. Optical fiber 13, which terminates adjacent to tip 26 of the catheter, enables laser radiation to be delivered to the abnormal conduction tissue. The laser radiation causes the tissue to vaporize and results in ablation of the conduction tissue. This will be described in more detail in connection with FIGS. 8 and 9.

FIG. 3 illustrates an embodiment of a laser catheter probe 34 in accordance with the invention. As shown, the catheter, which may be a generally circular tubular member, may be divided into first and second channels 32 and 34, respectively, by means of an internal partition or wall 36. Channel 32, which is preferably open at the tip 38 of the catheter, may carry a steerable guide wire 40 to facilitate threading of the catheter through the blood vessels, and channel 34 of the catheter may carry the optical fiber 13. As shown, the distal end of the optical fiber may terminate in a spherical beam focusing microlens 42 which is mounted at the tip 38 of the catheter. The microlens may be held in place by internal wall 36 and the external side wall 44 of the catheter body. As shown, the microlens is preferably positioned such that it bulges slightly outwardly from the tip 38.

Microlens 42 may comprise a sapphire ball attached to the end of the optical fiber or may comprise a ball of silica formed directly on the fiber as melting the tip into a spherical lens using the heat from a laser which is reflected back off the tip. This may be done in a furnace with graphite that is ignited by the laser beam. The microlens causes the laser beam exiting from the end of the optical fiber to be dispersed so that only a portion of the beam exits from the tip of the catheter. The remaining portion of the beam is dispersed or scattered back into the catheter tip itself. The catheter tip may be formed of metal or other heat conductive material so that the portion of the beam dispersed into the tip produces heating of the tip (for a reason to be described shortly). Alternatively, the catheter tip illustrated in FIG. 3 may be formed of plastic and fitted with a metal sleeve which absorbs the scattered radiation and heats up.

The catheter tip of FIG. 3 may have a sidewall thickness of the order 100μ (microns), the optical fiber may have a thickness of the order of 150μ, and the diameter of the catheter at its tip may be of the order of 1000 μ. As may be appreciated, these dimensions make the catheter especially well adapted for threading through smaller vessels such as cardiac arteries.

Figure 4:
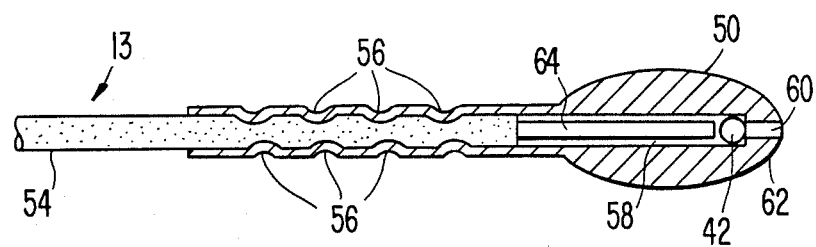
FIG. 4 is a partial sectional view of another embodiment of a laser probe in accordance with the invention, the figure illustrating an end cap disposed on the distal end of an optical fiber.
Figure 5:
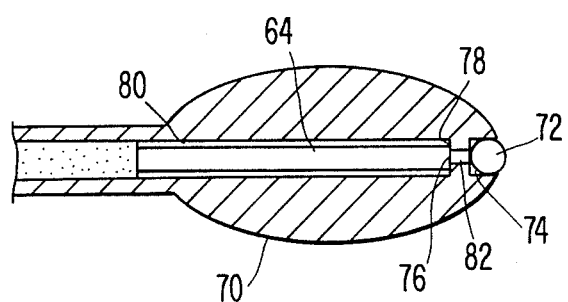
FIG. 5 is an enlarged sectional view of an alternate form of the end cap of the laser probe of FIG. 4.

FIGS. 4 and 5 illustrate alternative embodiments of a laser probe in accordance with the invention which is especially well adapted for recanalizing obstructed arteries. As shown in FIG. 4, the distal end of an optical fiber 13 may be fitted with an elliptically shaped end cap 50 formed of heat conductive material, such as stainless steel. The end cap may have tubular shaped neck 52 with a bore 58 which extends into the body of the end cap and which receives the optical fiber. The end cap may be attached to the optical fiber by crimping the neck onto the fiber cladding 54, as shown at 56. The end cap bore 58 is preferably coaxial with the axis of the end cap and may communicate with a somewhat smaller diameter bore 60 which extends to the tip 62 of the end cap, as shown. As also shown in the figure, the cladding 54 may be stripped from the core 64 of the optical fiber, and the fiber core may terminate so that its end is positioned a short distance from a spherical microlens 42 located within bore 58 adjacent to bore 60. As previously described, the microlens may comprise a solid spherical ball of sapphire.

The probe of FIG. 4 is adapted to extend beyond the tip of a standard flexible catheter (not illustrated). Preferably, the probe is connected to the catheter tip by a coil of steel wire or the like which encircles the optical fiber and has one end spot welded to the proximal end of neck 52 (the left end in FIG. 4) and has its opposite end spot welded to a metal sleeve fixed to the catheter tip. The coil of wire facilitates the alignment of the probe with the catheter tip and with the lumen of the vessel, while affording sufficient mechanical strength to enable pressure exerted on the catheter to be transmitted to the probe. The diameter of end cap 50 may be of the order of 2 mm at its largest point. The optical fiber may be a 300 μ core fiber; and bore 60 may have a diameter of the order of 250 μ.

In operation, the catheter carrying the probe of FIG. 4 is threaded through a blood vessel until the tip 62 of the probe contacts an obstruction in the vessel. The metal end cap conveniently permits viewing of the probe by making it visible on fluoroscopy, and facilitates advancement of the catheter and placement of the probe at the obstruction. The probe may also be incorporated into an angioscope catheter, if desired. Once the probe is in position, the laser supplying energy to optical fiber 13 may be pulsed in a systematic step-wise fashion using a dosimetric matrix. Beginning at 1 watt, as measured at the fiber tip, power may be incrementally increased in 1 watt increments up to a total of 8 watts. Initially, the pulse duration may be 1 second, and the interval between pulses 0.2 seconds. When an obstruction is penetrated at a specific power level, this power is held constant. If no penetration occurs at 12 watts of power and 1 second pulses, the pulse duration may be increased in 1 second intervals up to a total of 10 seconds per pulse. If penetration of the obstruction is still not possible, the procedure may be terminated.

The construction of the probe of FIG. 4 is such that only a portion of the laser beam carried by the optical fiber is emitted from the end cap and, therefore, only a portion of the laser energy is directly applied to the obstruction. The exposed portion of the fiber core within the end cap, the spherical microlens 42, and the spacing between the lens and the tip of the fiber core, causes most of the laser beam to be dispersed into the metal end cap, which produces heating of the end cap. This is a significant factor in avoiding perforation of the vessel wall. The power density in a focused laser beam may be quite high and if the focused beam directly impinges upon a vessel wall, it could possibly burn through the wall quite rapidly. The invention avoids this by limiting the amount of direct incident laser radiation on tissue, and achieves significantly improved results by employing a combination of direct incident radiation for vaporizing a small portion of the obstruction in contact with the probe tip, thermal melting of the obstruction by contact with the heated end cap, and mechanical pressure against the obstruction. While only a small amount of the obstruction is vaporized by the portion of the laser beam emitted from channel 60 of the probe, it has been found that this facilitates passage of the probe tip through the obstruction and, significantly, reduces the mechanical pressure required for penetration. This is important in enabling recanalization of smaller, tortuous arteries, such as cardiac arteries, as well as the removal of obstructions located at a substantial distance from the entry point from the catheter. Also, the rather small diameter of the probe, and the flexibility of the catheter which carries it, facilitates its use in the smaller vessels. The elliptical shape of the end cap is advantageous in assisting in the alignment of the probe along the center line of the vessel lumen.

Preferably, the end cap 50 of the probe is coated with Teflon or other slippery heat transmitting substance such as silicone to minimize sticking of the heated probe to tissue, which can result in tearing of the vessel and a thrombosis upon movement of the probe. It is also desirable to control the laser power such that the temperature of the probe end cap does not exceed about 350° C. This temperature is sufficient to enable burning through an obstruction while minimizing sticking of tissue to the end cap. Controlling the temperature may be accomplished either by calibrating the temperature rise of the probe as a function of the input power for different vessel flow rates, or by embedding within the end cap a thermocouple to afford direct monitoring of the probe temperature. Control of the probe temperature also enables the size of the channel through the obstruction to be controlled.

FIG. 5 illustrates a somewhat modified end cap 70 which may be employed in the probe of FIG. 4. The principal difference between the two end caps is that the spherical microlens 42 of the end cap of FIG. 4 is recessed within the probe and is connected to the probe tip via channel 60, whereas in end cap 70 the spherical microlens 72 is mounted directly at the tip within a recess 74 such that the lens bulges slightly outwardly beyond the tip, as shown. The distal end 76 of fiber core 64 may abut an end wall 78 of the end cap bore 80, and may communicate with recess 74 and the microlens via a smaller diameter channel 82. The length of channel 82 may be of the order of 1 mm, which allows dispersion of a portion of the beam leaving the distal end of the fiber into the end cap. Lens 72 focuses a small portion of the beam passing through channel 82 outwardly from the tip of the end cap, and disperses the remaining portion of the beam back into the end cap for heating it. Lens 72 may be held in place by crimping the metal edges of recess 74 into contact with its surface. An advantage of the probe of FIG. 5 over that illustrated in FIG. 4 is that there is no open channel, such as 60, into which debris can enter. Therefore, it affords better optical stability.

Figure 6:
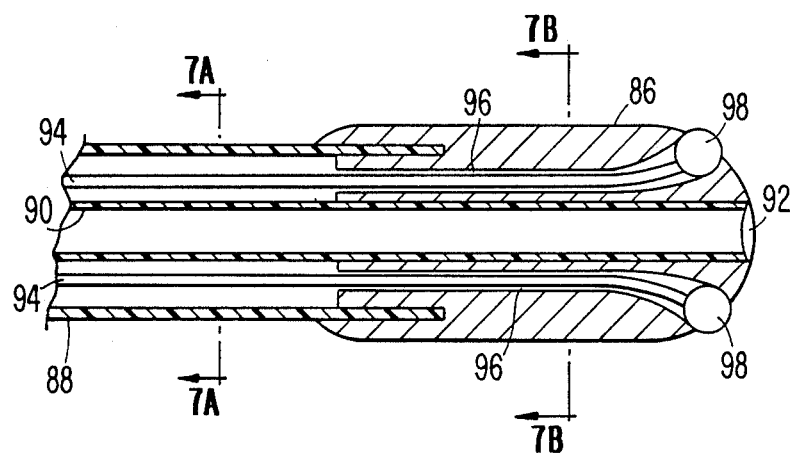
FIG. 6 is a partial sectional view of yet another embodiment of a laser probe in accordance with the invention.
Figure 7A:
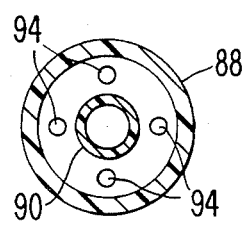
FIGS. 7A and 7B are, respectively, transverse sectional views taken approximately along the lines 7A—7A and 7B—7B of FIG. 6.
Figure 7B:
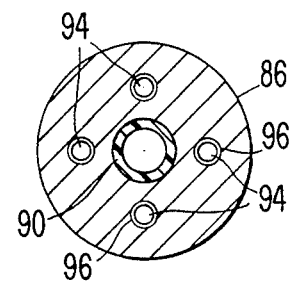

FIGS. 6, 7A and 7B illustrate another embodiment of the invention. In this embodiment, the heat conductive end cap 86, which may be of steel and coated as previously described, is disposed directly on the distal end of a catheter 88. The catheter may have a centrally located tubular member 90 therethrough which forms a channel for a guide wire (not illustrated). As shown, the tubular channel may extend through the end cap 86 and terminate in an opening 92 at the tip of the end cap. The catheter may carry a plurality, four, for example, of optical fibers 94 which extend through corresponding channels 96 in the end cap and terminate in corresponding spherical microlenses 98. Each spherical lens may comprise a sapphire ball connected to the end of its corresponding fiber, or may comprise a ball of silica formed by melting the end of the fiber as previously described. The lenses are preferably symmetrically disposed about the opening 92 in the tip of the end cap, and may bulge slightly outwardly from the surface of the end cap as shown. The channels 96 which carry the optical fibers may widen adjacent to the surface of the end cap to accommodate the spherical lenses, and are preferably angled outwardly relative to the center line axis of the end cap, as shown, so that the optical fibers are similarly angled relative to the center line at their connection to the lenses. This arrangement directs the portions of the laser beams emitted by the lenses 98 outwardly from the end cap at an acute angle to its center line and enables the catheter tip to produce a channel through an obstruction which is wider than the actual diameter of the end cap.

As previously described, in connection with the other embodiments, the spherical lenses disperse a portion of the laser beams back into the end cap in order to heat it, and the channel through the obstruction is produced by a combination of direct incident laser radiation, thermal melting caused by contact with the heated tip, and mechanical pressure. In addition, as previously described, the end cap may be coated with Teflon or impregnated with a substance such as silicone to minimize sticking of the heated end cap to tissue, and a thermocouple may be embedded in the end cap to permit the temperature of the end cap to be monitored and the laser power to be controlled so that a desired temperature is produced.

Catheter 88 may have a diameter of the order of 1200μ, and end cap 86 may have a diameter of the order of 1500μ, which enables it to be used conveniently in smaller vessels. The shape of the end cap also facilitates its alignment and positioning within the lumen of the vessel. The optical fibers 94 may be 150μ diameter fibers and the inner diameter of tubular member 90 may be of the order of 400μ. It will be appreciated that although four optical fibers are illustrated, more or less than this may be used. Also, a single laser may be used as a source of laser radiation for all the fibers by employing a conventional mechanical beam diverter for diverting the laser beam into the fibers.

Figure 8:
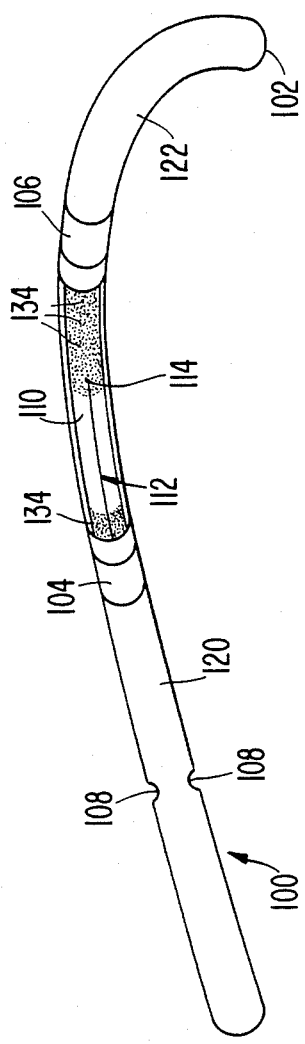
FIG. 8 is a perspective view of a portion of an embodiment of an optical fiber/diffuser catheter apparatus in accordance with the invention which is adapted to detect and destroy conduction pathways within the heart.
Figure 9:
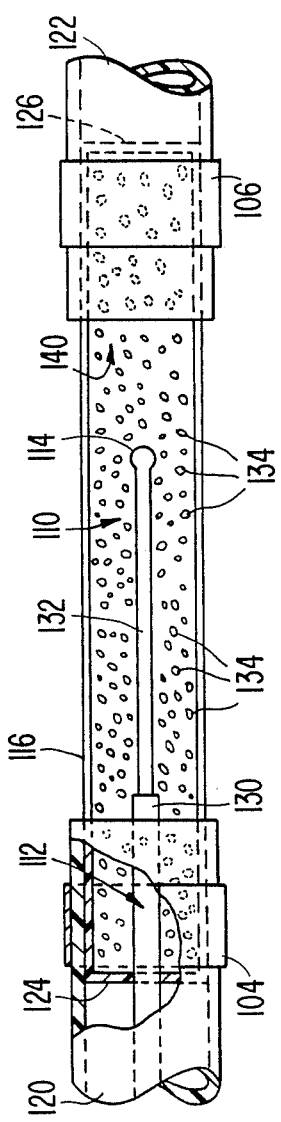
FIG. 9 is an enlarged elevational view, partially broken away and partially in section, of a portion of the apparatus of FIG. 8.

FIGS. 8 and 9 illustrate a preferred form of a diffuser catheter in accordance with the invention which is particularly well adapted for the detection, localization and ablation of normal and abnormal conduction tissue in the heart. Abnormal conduction via "accessory pathways" leads to pre-excitation syndromes. In addition, foci of recurrent ventricular tachycardia can be ablated. Present methods of treatment of such conditions involve a complicated surgical technique known as "cardiac mapping" which involves opening the chest and placing a net around the heart that detects foci of irritation, which can then be frozen or excised by surgical incision. The diffuser catheter of FIG. 8 enables such conduction tissue to be precisely located and destroyed using laser radiation while avoiding the necessity of complicated surgical procedures.

Referring to FIG. 8, the diffuser catheter comprises a tubular catheter body 100 having a distal end 102 which is closed. The distal end 102 is closed in the sense that light is not emitted therefrom and it does not include any openings for other components, this being clearly illustrated in FIG. 8. The catheter is shaped in a well-known manner so as to sit within the heart at locations where conduction tissue is generally found. A pair of spaced metal electrodes 104 and 106 may be disposed about the catheter body on its peripheral surface adjacent to end 102. The electrodes may be connected by electrical conduction leads which extend through the tubular catheter body to an electrocardiogram (not illustrated) for detection and localization of the conduction tissue. Side ports 108 through the sidewall of the catheter body may also be provided to enable contrast solution or the like to be ejected. A laser radiation transparent window 110 may be located in the sidewall of the catheter body between the two spaced electrodes, and the catheter may carry an optical fiber 112 which terminates in a microlens 114 adjacent to the window.

FIG. 9 illustrates in more detail a preferred form of construction of the diffuser catheter. As shown, window 110 may comprise a hollow closed tube 116 which is coaxially disposed between first and second tubular catheter sections 120 and 122, respectively, with the ends 124 and 126 of the tube fitted tightly within the tubular sections. The optical fiber 112 may enter the interior of the tube through end 124, and the cladding 130 of the optical fiber may be stripped from the core 132 so as to expose a length of the core adjacent to the window. As previously noted, the fiber may terminate in a microlens 114, which may comprise a sphere of silica or sapphire as previously described. The laser beam carried by the optical fiber is emitted over the exposed length (i.e., uncovered by cladding) of the fiber core, and the microlens causes dispersion of the beam exiting the fiber.

The interior of tube 116 may be filled with a plurality microspheres 134, which cause further dispersion of the laser beam emitted from the optical fiber. (In FIGS. 8 and 9, the microspheres have not been shown as filling the tube so as to avoid cluttering of the figures.) The microspheres may be either of glass or plastic, although glass is preferred, since it is better able to withstand the heat produced by the laser radiation. Tube 116 is preferably formed of quartz or sapphire for the same reason. A semicylindrical portion 140 of the interior surface of the tube, such as one-half of its interior surface, may be mirrored so as to reflect the laser radiation impinging thereon. This enables all of the laser radiation to be directed outwardly through only one side of the tube, i.e., through the window 110, so that only the tissue adjacent to that side of the tube is exposed to the radiation and treated. In addition, microlens 114 may have a slanted cut at 45°, for example, so as to direct the beam exiting from the lens outwardly through the window.

In use, the catheter may be threaded through an artery into the heart. Upon detecting the presence of conduction tissue between the electrodes using the electrocardiogram, the laser source may be energized to supply laser energy. The laser beam emitted from the exposed length of fiber core 132 and microlens 114 is dispersed by the microspheres and reflected outwardly through the window into the adjacent tissue. The laser radiation causes ablation of the adjacent conduction tissue and destroys the conduction pathways. The electrodes permit monitoring of the conduction state of the tissue and appropriate control of the laser source.

In using the invention for recanalization of vessels obstructed by deposits of plaque, ablation of conduction tissue, etc. various sensitizing agents may be employed which preferentially increase the absorption of the laser radiation by the plaque or other tissue to be treated as opposed to the surrounding tissue, and thereby enhance its removal. It has been discovered that, for example, that whole blood itself is a suitable sensitizing agent. This result is highly unexpected in view of earlier indications that blood should be evacuated prior to recanalization with laser radiation. Other substances which efficiently sensitize plaque for preferential absorption of laser radiation include hematoporphyrin derivative (HPD), fluorescein, carbol fuchsin, methylene blue, Evans blue, Trypan blue, quinicrine hydrochloride, neutral red, Sudan black, tetracycline, para-aminobenzoic acid, acridine orange and others. An amount of the sensitizing agent sufficient to sensitize the plaque for preferential absorption of the laser radiation may be administered by intravenous injection to the patient prior to lasing. Preferably, the agent is administered 24 to 48 hours prior to recanalization. When utilizing HPD, preferably about 2.5 to about 4 mg/kg of body weight is administered to the patient.

Any conventional laser which produces radiation that is capable of being carried an optical fiber may be employed in practicing the invention. For example, argon and Nd-YAG lasers are commonly available and may be used. Also, conventional catheters, including those employed for angioscopy, in some instances modified as taught herein, may be used in practicing the invention.

In addition to recanalization of vessels and ablation of conduction tissue, the invention has other uses. In some cases, it is necessary occlude, i.e., close, an undesirable cardiovascular channel. For example, in a premature infant with patent ductus arteriosus, the existence of a connection between the pulmonary artery and the aorta which produces this condition often leads to heart failure. The invention may be employed to occlude this undesirable channel to avoid the necessity for the currently utilized thoracotomy to tie off this connection. Another use of this invention is for the revascularization of cardiovascular tissue. In certain congenital cardiac conditions, it is often necessary to open conduits or channels between certain cardiac chambers, such as the atria. Thus, an artificially created atrial septal defect (ASD) may be critical and life saving. The invention may be utilized to open such a window or flap between the atrial chambers by burning through the tissues necessary to create the desired channel.

While preferred embodiments of the invention have been shown and described, it will be appreciated by those skilled in the art that changes may be made in these embodiments without departing from the principles and the spirit of the invention, the scope of which is defined in the appended claims.

I claim:

1. Apparatus for treating cardiac conditions with laser radiation comprising a catheter adapted to be inserted into a blood vessel and threaded through the blood vessel to a region to be treated, the catheter comprising a tubular body having a window of laser radiation transparent material formed in a sidewell thereof; an optical fiber for guiding a laser beam disposed within the catheter, the optical fiber having an end terminating adjacent to said window; and lens means on the end of the optical fiber for dispersing a laser beam guided by the optical fiber sideways outwardly through said window for treating tissue adjacent to the window and wherein said window comprises a closed tubular section of said transparent material which is coaxially disposed between a first catheter body section and a second catheter body section, said optical fiber entering the closed tubular section and terminating therein and wherein said closed tubular section has a cylindrical inner surface which is mirrored except for a part thereof which forms said window so as to reflect the laser beam from the optical fiber outwardly through the window.

2. Apparatus for treating cardiac conditions with laser radiation comprising a catheter adapted to be inserted into a blood vessel and threaded through the blood vessel to a region to be treated, the catheter comprising a tubular body having a window of laser radiation transparent material formed in a sidewall thereof; an optical fiber for guiding a laser beam disposed within the catheter, the optical fiber having an end terminating adjacent to said window; and lens means on the end of the optical fiber for dispersing a laser beam guided by the optical fiber sideways outwardly through said window for treating tissue adjacent to the window, and further comprising first and second electrode means disposed about the tubular catheter body on opposite sides of the window for detecting the presence of conductive tissue adjacent to said window.

3. The apparatus of claim 2 wherein said catheter has a closed distal end.

4. The apparatus of claim 2 wherein said window comprises a closed tubular section of said transparent material which is coaxially disposed between a first catheter body section and second catheter body section, and optical fiber entering the closed tubular section and terminating therein.

5. The apparatus of claim 4 further comprising radiation-dispersing microspheres disposed within the closed tubular section for dispersing the laser beam from the optical fiber.

6. The apparatus of claim 5 wherein said microspheres are made of material selected from the group comprising glass and plastic.

7. The apparatus of claim 2 wherein said optical fiber includes a core and a cladding, and wherein said core is exposed along a length thereof adjacent to the window such that alight from a laser beam may pass from the exposed length of the core to the window.

8. A method for the ablation of electrical conduction tissue in a heart comprising threading a catheter through a blood vessel into the heart, the catheter carrying an optical fiber and having first and second spaced electrodes located on a peripheral surface of the catheter; positioning the catheter such that the electrodes contact tissue; detecting the presence of electrical conduction tissue in contact with the electrodes; supplying laser energy to the optical fiber for transmission to the location of the electrodes; and causing the laser energy transmitted by the optical fiber to be emitted sideways outwardly from a part of the catheter disposed between the spaced electrodes and into said conduction tissue.

9. The method of claim 8, wherein said causing comprises dispersing the laser energy emitted from a length of the optical fiber located between the spaced electrodes outwardly through a window in a sidewall of the catheter.

10. The method of claim 9, wherein said dispersing comprises reflecting the laser energy such that all of the laser energy is emitted through said window.

* * * * *

UNITED STATES PATENT AND TRADEMARK OFFICE
CERTIFICATE OF CORRECTION

PATENT NO. : 4,860,743
DATED : August 29, 1989
INVENTOR(S) : GEORGE S. ABELA

It is certified that error appears in the above-identified patent and that said Letters Patent is hereby corrected as shown below:

Claim 1, column 11, line 15, "sidewell" should read --sidewall--;

Claim 4, column 12, line 9, "and" (first occurrence), should read --said--;

Claim 7, column 12, line 21, "alight" should read --light--.

Signed and Sealed this

Tenth Day of July, 1990

Attest:

HARRY F. MANBECK, JR.

*Attesting Officer*     *Commissioner of Patents and Trademarks*